United States Patent
Albrecht et al.

(10) Patent No.: US 6,299,872 B1
(45) Date of Patent: Oct. 9, 2001

(54) COMBINATION THERAPY FOR CHRONIC HEPATITIS C INFECTION

(75) Inventors: Janice K. Albrecht, Winter Park, FL (US); Paul C. Grint, Basking Ridge, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/563,649

(22) Filed: May 2, 2000

Related U.S. Application Data

(63) Continuation of application No. 08/444,584, filed on May 19, 1995.

(51) Int. Cl.$^7$ .................................................. A61K 38/21
(52) U.S. Cl. .................................................................. 424/85.7
(58) Field of Search ................................. 424/85.7, 85.4; 514/2; 530/351

(56) References Cited

U.S. PATENT DOCUMENTS

| Re. 29,835 | 11/1978 | Witkowksi et al. | 536/26.11 |
|---|---|---|---|
| 4,211,771 | 7/1980 | Witkowski et al. | 514/43 |
| 4,530,901 | 7/1985 | Witkowski et al. | 435/69.51 |

OTHER PUBLICATIONS

Bizollon et al., Benefit of the combination interferon (IFN)–ribavirin in the treatment of C viral reinfections following hepatic transplantation (HT), Revue Francaise de Castro– enterologie (1994) 30(297), Case No. ID0492.*
Brillanti et al., Gastroenterology (1994) 107:812–817.*
Carreno et al., J. Med. Virol. (1992) 37(3): 215–219.*
Drinkard et al., A Phase I trial of intensive concomitant chemoradiotherapy with cisplatin dose escalation in advanced malignancies of the chest (Meeting Abstract). 4th International Congress on Anti–Cancer Chemotherapy. Feb. 2–5, 1993, Paris, France.*
Kakumu et al., Gastroenterology (1993) 105:507–512.*
Lai et al., Treatment of Chronic Active Hepatitis C infection with a Combination of Roferon–A and Ribavirin (Meeting Abstract), 9th Biennial Scientific Meeting Asian Pacific Association for the Study of the Liver. Jan. 27, 1994, Kuala Lumpur, Malaysia.*

Nozaki et al., Rinsho Ketsueki. Japanese Journal of Clinical Hematology, (1993) 34(2):232–234.*
Cavaletto, L et al, Congress Proceedings from Ital. J. Gastrenterol., 25:443–68, Abstract at p. 452 (Venezia, Nov. 11–13, 1993).
Braconier et al, Scan. J. Infect. Dis. 27:325–9 (1995).
Schvarcz et al, J. Med. Virol. 46:43–47 (1995).
Brouwer et al, ISSN 21:Suppl 1, S1–S198 (1994).
The Merck Index, 11th Ed., Compound No. 8199.
Hepatology, vol. 20, No. 4, Pt. 2, Abstract Nos. 440 and 441.
Bisceglie et al, Hepatology 16:649–654 (1992).
Kakumu et al, Gastroenterology 105:507–512 (1993).
Marcellin et al, Baillere's Clin. Gastroenter. 8:233–253 (1994).
Brillanti et al, J. Hepatol. 18(Suppl. 1):S101 (Abstract No. T–69) (1993).
Sambataro, J. Hepatol. 18(Suppl. 1):S167 (Abstract No. T–377) (1993).
Wu et al, Antiviral Res. (Suppl. 1), Abstract No. 228 (1993).
Brillanti et al, Gastroenterology 107:812–817 (1994).
Brillanti et al, Hepatology 18:150A, Abstract No. 375 (1993).
Lai et al, Hepatology 18:93A, Abstract No. 146 (1993).
Chemello et al, J. Hepatol. 21 (Suppl. 1):S12 (Abstract No. GS 5/29) (1994).
Brouwer et al, J. Hepatol. 21 (Suppl. 1):S17 (Abstract No. WP2/08) (1994).
Package Insert for Intron A Interferon Alpha–2b Recombinant, 1992, Schering Corporation, Kenilworth, NJ.
Revue Francais de Castro–Enterologie, Apr. 1994, No. 297 (English Translation).

* cited by examiner

Primary Examiner—Karen Cochrane Carlson
Assistant Examiner—Stephen Tu
(74) Attorney, Agent, or Firm—Donald W. Wyatt

(57) ABSTRACT

There is disclosed a method for treating chronic hepatitis C infection in patients in need of such treating comprising administering an amount of alpha interferon in association with an amount of ribavirin effective to treat chronic hepatitis C infection with the absence or substantial reduction of side effects associated with administration of ribavirin and alpha interferon.

7 Claims, No Drawings

COMBINATION THERAPY FOR CHRONIC HEPATITIS C INFECTION

This application is a continuation of U.S. Ser. No. 08/444,584 filed May 19, 1995.

Throughout this disclosure, various publications, patents and patent applications are referenced. The disclosures of these publications, patents and patent applications are herein incorporated by reference.

Chronic infection with hepatitis C virus is an insidious and slow-progressing disease having a significant impact on the quality of life. It can eventually result in cirrhosis of the liver, decompensated liver disease and/or hepatocelluar carcinoma.

Alpha interferon monotherapy is commonly used to treat chronic hepatitis C infection. However this treatment is not always effective and sometimes results in intolerable side effects related to the dosage and duration of therapy. Ribavirin has been proposed as a monotherapy treatment for chronic hepatitis C infection (Thomas et al. AASLD Abstracts, Hepatology Vol. 20, NO. 4, Pt 2, Number 440, 1994). However, this monotherapy treatment has usually been found relatively ineffective and has its own undesirable side effects.

Combination therapy of alpha interferon and ribavirin has been proposed (Lai, et al. Symposium to the 9th Biennial Scientific Meeting Asian Pacific Association for the Study of the Liver. 1994). Preliminary results suggest that the combination therapy may be more effective than either monotherapy. However at the proposed dosages, undesirable side effects have still been encountered.

There is a need for a method for treating chronic hepatitis C infection with a combination of alpha interferon and ribavirin in the substantial absence of side effects normally associated with either compound.

SUMMARY OF THE INVENTION

This invention may be summarized as a method for treating chronic hepatitis C infection in patients in need of such treating comprising administering an amount of alpha interferon in association with an amount of ribavirin effective to treat hepatitis C in the absence or substantial reduction of side effects associated with ribavirin and alpha interferon.

DETAILED DESCRIPTION

All references cited herein are incorporated herein by reference.

The term "alpha interferon" as used herein means the family of highly homologous species-specific proteins that inhibit viral replication and cellular proliferation and modulate immune response. Typical suitable alpha interferons include but are not limited to recombinant interferon alpha-2b such as Intron-A interferon available from Schering Corporation, Kenilworth, N.J., recombinant interferon alpha-2a such as Roferon A interferon available from Hoffmann-La Roche, Nutley, N.J., recombinant interferon alpha-2C such as Berofor alpha 2 interferon available from Boehringer Ingelheim Pharmaceutical, Inc., Ridgefield, Conn., interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain, or a consensus alpha interferon available from Amgen, Inc., Newbury Park, Calif., or interferon alpha-n3 a mixture of natural alpha interferons made by Interferon Sciences and available from the Purdue Frederick Co., Norwalk, Conn., under the Alferon Tradename. The use of interferon alpha-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,530,901. Of course the term alpha interferon includes the obvious equivalents thereto such as certain beta interferons known to have properties similar to alpha interferon.

Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771.

A person suffering from chronic hepatitis C infection may exhibit one or more of the following signs or symptoms:

(a) elevated ALT, (b) positive test for anti-HCV antibodies, (c) presence of HCV as demonstrated by a positive test for HCV-RNA, (d) clinical stigmata of chronic liver disease, (e) hepatocelluar damage.

To practice the invention, alpha interferon (hereinafter α-IFN) and ribavirin are administered to the patient exhibiting one of more of the above signs or symptoms in amounts sufficient to eliminate or at least alleviate one or more of the signs or symptoms.

In prior treatment of chronic hepatitis C infection with α-IFN monotherapy, α-IFN has been administered in dosages of about 3 to 10 million international units (IU) thrice weekly. Alternatively 3 to 10 million IU of α-IFN has been administered QOD (every other day) or daily. The duration of the prior dosages has been from 12 to 24 months. This amount and duration of α-IFN monotherapy alleviates symptoms of hepatitis C in some of the patients, but it causes undesirable side effects, e.g. flu-like symptoms, in some.

The preferred dosage of α-IFN for practicing the combination therapy of this invention is less than the prior amount, that is, less than 3 million IU, more preferably 1 to 2 million IU administered thrice weekly, QOD, or daily. Alternatively the prior dosage of 3 to 10 million IU administered thrice weekly, QOD or daily may be administered for a shorter duration, that is from 6 to 12 months. In either case, reduced side effects of α-IFN are expected, because of the reduced dosage or duration.

In prior treatment of chronic hepatitis C infection with ribavirin monotherapy the usual dosage of ribavirin has been 1000 to 1200 mg administered daily. This amount of ribavirin has been found to be marginally effective in alleviating symptoms in a small percentage of the patients, but it causes the undesirable side effect of anemia.

The preferred dosage of ribavirin for practicing this invention is about 400 to 1000 mg per day, more preferably 500 to 800. This daily dosage may be administered once per day in a single dose or in divided doses.

The ribavirin is administered to the patient in association with the α-IFN, that is, the α-IFN dose is administered during the same period of time that the patient receives doses of ribavirin. At present (α-IFN formulations are not effective when administered orally, so the preferred method of administering the α-IFN is parenterally, preferably by subcutaneous, IV, or IM, injection. The ribavirin may be administered orally in capsule or tablet form in association with the parenteral administration of α-IFN. Of course other types of administration of both medicaments, as they become available are contemplated, such as by nasal spray, transdermally, by suppository, by sustained release dosage form, etc. Any form of administration will work so long as the proper dosages are delivered without destroying the active ingredient.

The effectiveness of treatment may be determined by controlled clinical trials of the combination therapy versus monotherapy. The efficacy of the combination therapy in alleviating the signs and symptoms of chronic hepatitis C infection and the frequency and severity of the side effects will be compared with previous α-IFN and ribavirin monotherapy. Three populations suffering from chronic hepatitis C infection will be evaluated:

1. Patients previously untreated.
2. Patients previously treated with interferon or ribavirin and who had subsequently relapsed.
3. Patients who were non-responsive to previous treatment with interferon or ribavirin.

The effectiveness of the combination therapy will be determined by the extent to which the previously described signs and symptoms of chronic hepatitis are alleviated and the extent to which the normal side effects of α-IFN and ribavirin are eliminated or substantially reduced. The reduction or elimination of side effects will be accomplished by reduced dosage or dosage duration or both compared to the previous monotherapies.

The normal side effects for α-IFN are listed in the package insert for INTRON-A interferon alfa-2b, recombinant, published 10/94 by Schering Corporation, Kenilworth N.J. The are primarily flu-like symptoms such as fever, head ache, chills, myalgia, fatigue, etc. and central nervous system related symptoms such as depression, paresthesia, impaired concentration, etc.

The normal side effect of ribavirin is hemolytic anemia

What is claimed is:

1. A method for treating Hepatitis C, comprising treating a patient having symptoms of Hepatitis C infection with a combination of interferon alpha and ribavirin and said interferon alpha is administered to said patient in less than 3 million international units dosed once weekly to reduce said symptoms of Hepatitis C infection.

2. The method of claim 1, wherein said interferon alpha is interferon alpha2a.

3. The method of claim 2, wherein dosage of said ribavirin is between 400 and 1000 milligrams per day, inclusive.

4. The method of claim 3, wherein said dosage of said ribavirin is between 500 and 800 milligrams per day, inclusive.

5. The method of claim 1, wherein said interferon alpha is interferon alpha2b.

6. The method of claim 5, wherein dosage of said ribavirin is between 400 and 1000 milligrams per day, inclusive.

7. The method of claim 6, wherein said dosage of said ribavirin is between 500 and 800 milligrams per day, inclusive.

* * * * *